US011446074B2

(12) United States Patent
Kollmann et al.

(10) Patent No.: US 11,446,074 B2
(45) Date of Patent: Sep. 20, 2022

(54) CRYOABLATION SYSTEM WITH MAGNETIC RESONANCE IMAGING DETECTION

(71) Applicant: Biocompatibles UK Limited, Camberley (GB)

(72) Inventors: Daniel T. Kollmann, Andover, MN (US); Timothy J. Davis, Coon Rapids, MN (US); Satish Ramadhyani, Minneapolis, MN (US); Luan T. Chan, Coon Rapids, MN (US)

(73) Assignee: BIOCOMPATIBLES UK LIMITED, Camberley (GB)

( * ) Notice: Subject to any disclaimer, the term of this patent is extended or adjusted under 35 U.S.C. 154(b) by 891 days.

(21) Appl. No.: 16/189,263

(22) Filed: Nov. 13, 2018

(65) Prior Publication Data
US 2019/0142492 A1 May 16, 2019

Related U.S. Application Data

(60) Provisional application No. 62/585,262, filed on Nov. 13, 2017.

(51) Int. Cl.
*A61B 5/02* (2006.01)
*A61B 5/055* (2006.01)
(Continued)

(52) U.S. Cl.
CPC .............. *A61B 18/02* (2013.01); *A61B 5/055* (2013.01); *A61B 2018/00005* (2013.01);
(Continued)

(58) Field of Classification Search
CPC ........... A61B 2018/00005; A61B 2018/00017; A61B 2018/00041; A61B 2018/00577;
(Continued)

(56) References Cited

U.S. PATENT DOCUMENTS 3,910,277 A 10/1975 Zimmer
4,444,156 A 4/1984 Iwasaki et al.
(Continued)

FOREIGN PATENT DOCUMENTS

CA 2261177 C 5/2007
EP 0927542 A2 7/1999
(Continued)

OTHER PUBLICATIONS

Jurns, John M., "Flow of Sub-Cooled Cryogens through a Joule-Thomson Device: Investigation of Metastability Conditions" (2007). ETD Archive. 661. https://engagedscholarship.csuohio.edu/etdarchive/661 (Year: 2007).*

(Continued)

*Primary Examiner* — Eun Hwa Kim
(74) *Attorney, Agent, or Firm* — Faegre, Drinker, Biddle & Reath, LLP

(57) ABSTRACT

A magnetic resonance imaging (MRI) guided surgical system is provided that includes one or more surgical tools having components configured to develop reactive effects when exposed to MR signals generated by the MRI system. The system includes a control system that can determine whether the MR system is generating MR signals, and if the control system determines that the MR system is generating MR signals, mitigates the reactive effects of MR signals on components of the surgical tools. The system can include a cryoablation system with a cryoprobe having a probe shaft being made of a metallic material. If the control system determines that the MR system is generating MR signals, the control system can electrically disconnect the cryoprobe and/or ignore electrical signals generated by the electric heater in response to exposure to MR signals, and/or initiate a cooling operation of the probe shaft, whereby the cooling operation.

14 Claims, 5 Drawing Sheets

(51) Int. Cl.
*A61B 18/02* (2006.01)
*A61B 18/00* (2006.01)
*G01R 33/28* (2006.01)
*A61B 90/00* (2016.01)

(52) U.S. Cl.
CPC ........ *A61B 2018/00017* (2013.01); *A61B 2018/00041* (2013.01); *A61B 2018/00577* (2013.01); *A61B 2018/00744* (2013.01); *A61B 2018/00791* (2013.01); *A61B 2018/00803* (2013.01); *A61B 2018/0212* (2013.01); *A61B 2018/0262* (2013.01); *A61B 2018/0293* (2013.01); *A61B 2090/374* (2016.02); *G01R 33/285* (2013.01)

(58) Field of Classification Search
CPC ......... A61B 2018/00744; A61B 2018/00791; A61B 2018/00803; A61B 2018/0212; A61B 2018/0293; A61B 18/02; A61B 2090/374; G01R 33/285
See application file for complete search history.

(56) References Cited

U.S. PATENT DOCUMENTS

| | | | |
|---|---|---|---|
| 4,600,218 A | 7/1986 | Ross et al. | |
| 4,602,809 A | 7/1986 | Ross et al. | |
| 4,862,697 A | 9/1989 | Tugal et al. | |
| 5,522,870 A | 6/1996 | Ben-Zion | |
| 5,603,221 A | 2/1997 | Maytal | |
| 5,800,487 A | 9/1998 | Mikus et al. | |
| 5,800,488 A | 9/1998 | Crockett | |
| 5,916,212 A | 6/1999 | Baust et al. | |
| 5,978,697 A * | 11/1999 | Maytal | A61B 18/02 324/320 |
| 6,074,412 A | 6/2000 | Mikus et al. | |
| 6,270,476 B1 | 8/2001 | Santoianni et al. | |
| 6,505,629 B1 | 1/2003 | Mikus et al. | |
| 7,846,154 B2 | 12/2010 | Bliweis et al. | |
| 7,850,682 B2 | 12/2010 | Amir et al. | |
| 8,066,697 B2 | 11/2011 | Zvuloni et al. | |
| 2002/0010460 A1* | 1/2002 | Joye | A61B 18/0218 606/21 |
| 2002/0111615 A1 | 8/2002 | Cosman et al. | |
| 2003/0055416 A1 | 3/2003 | Damasco et al. | |
| 2004/0210212 A1 | 10/2004 | Maurice | |
| 2005/0010200 A1 | 1/2005 | Damasco et al. | |
| 2005/0065511 A1 | 3/2005 | Geistert | |
| 2005/0228367 A1 | 10/2005 | Abboud et al. | |
| 2006/0155267 A1 | 7/2006 | Berzak et al. | |
| 2007/0149959 A1 | 6/2007 | DeLonzor et al. | |
| 2009/0292280 A1 | 11/2009 | Cytron et al. | |
| 2010/0114275 A1 | 5/2010 | Min | |
| 2010/0134273 A1* | 6/2010 | Weiss | G01R 33/285 340/532 |
| 2010/0256620 A1 | 10/2010 | Maytal | |
| 2011/0022040 A1 | 1/2011 | Geiselhart | |
| 2011/0264084 A1 | 10/2011 | Reid | |
| 2012/0065630 A1 | 3/2012 | Berzak et al. | |
| 2012/0089136 A1 | 4/2012 | Levin et al. | |
| 2012/0265452 A1 | 10/2012 | Ramadhyani et al. | |
| 2012/0289953 A1 | 11/2012 | Berzak et al. | |
| 2013/0204241 A1 | 8/2013 | Baust | |
| 2014/0024909 A1 | 1/2014 | Vij et al. | |
| 2014/0135754 A1 | 5/2014 | Berzak et al. | |
| 2014/0194863 A1 | 7/2014 | Berzak et al. | |
| 2014/0232103 A1 | 8/2014 | Waugh | |
| 2016/0242835 A1 | 8/2016 | Ramadhyani et al. | |
| 2016/0249882 A1* | 9/2016 | Degertekin | A61B 1/05 600/424 |
| 2016/0367305 A1 | 12/2016 | Hareland | |

FOREIGN PATENT DOCUMENTS

| | | |
|---|---|---|
| EP | 925045 B1 | 4/2003 |
| GB | 2336781 A | 11/1999 |
| JP | 2012-529977 A | 11/2012 |
| WO | 2005000106 A2 | 1/2005 |
| WO | 2007/129310 A2 | 11/2007 |
| WO | 2014144626 A2 | 9/2014 |

OTHER PUBLICATIONS

International Search Report and Written Opinion received for PCT Patent Application No. PCT/IB2018/058774, dated Feb. 15, 2019, 15 pages.
JP Office Action dated Jan. 4, 2022 for JP Application No. 2020526280.

* cited by examiner

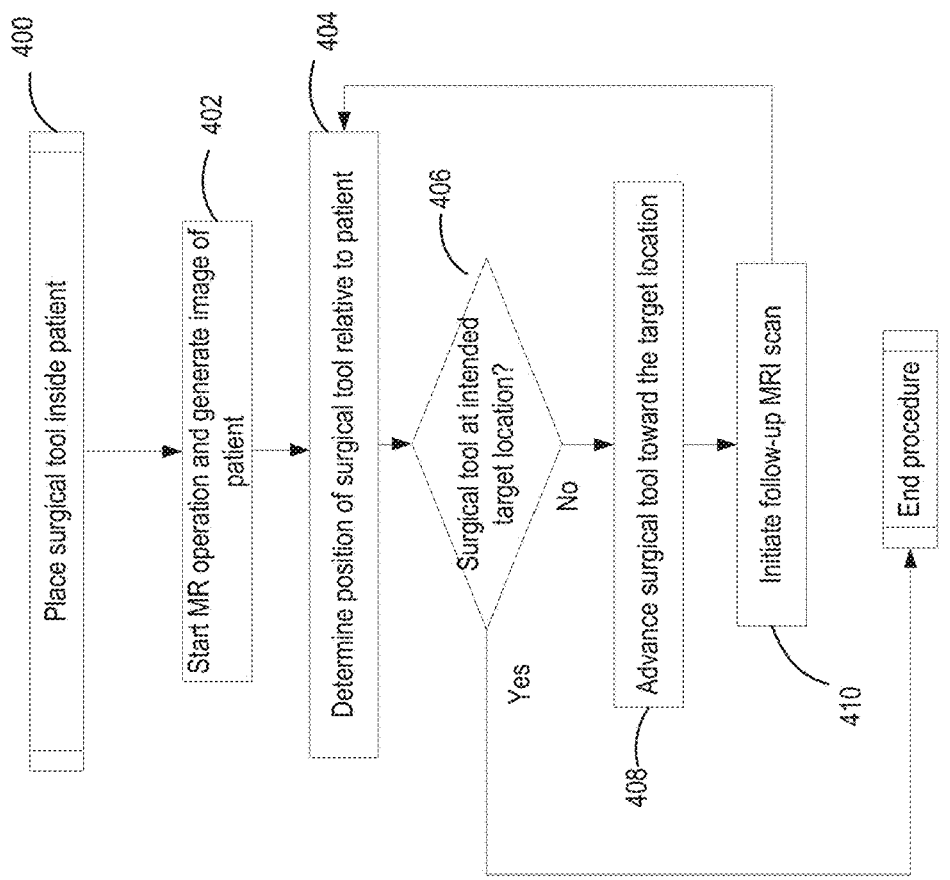
Fig. 4
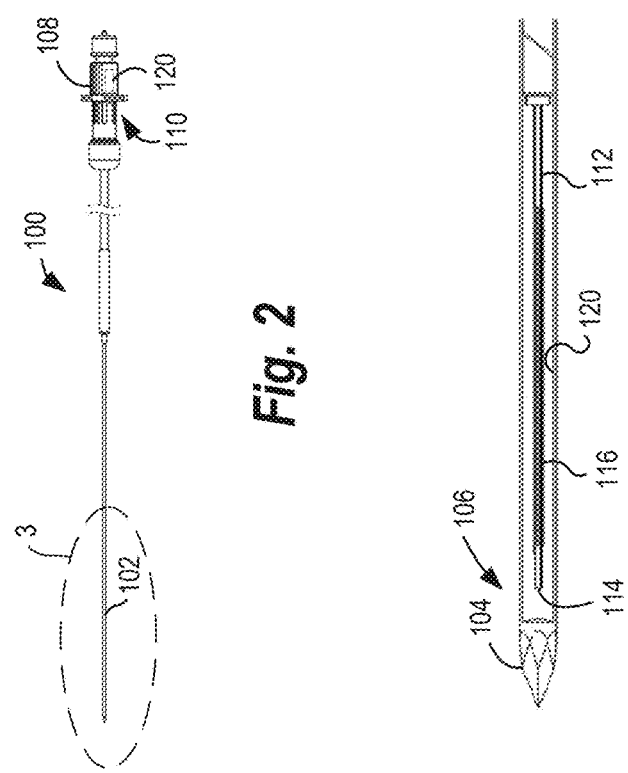
Fig. 2
Fig. 3

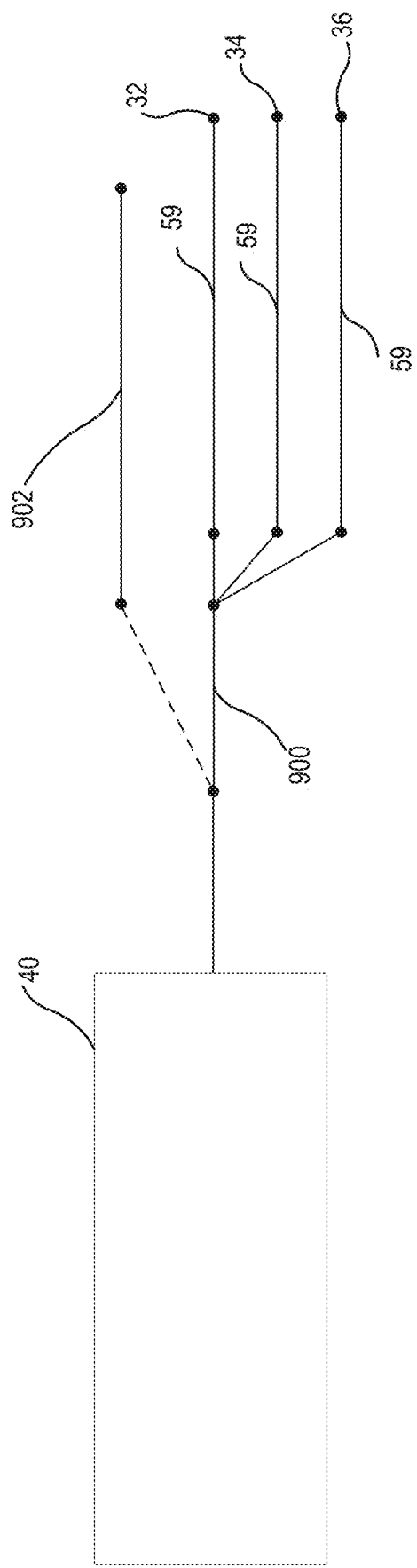

CRYOABLATION SYSTEM WITH MAGNETIC RESONANCE IMAGING DETECTION

CROSS REFERENCE TO RELATED APPLICATION

This application claims the benefit of U.S. Provisional Application No. 62/585,262, filed Nov. 13, 2017, the content of which is hereby incorporated by reference in its entirety.

BACKGROUND

Cryosurgical systems comprise one or more cryoprobe connected to one or more cryofluid sources. Such systems are described in the commonly-assigned patent, U.S. Pat. No. 8,066,697 and in published application, U.S. Pub. No. 2010/0256620 A1, the disclosure of which is hereby incorporated by reference in its entirety. In such cryosurgical systems, a cryofluid can be delivered from a cryofluid source to one or more cryoprobes. The cryoprobe can be cooled as a result of expansion of the cryofluid, thereby freezing tissue in the vicinity of a tip of the cryoprobe. Some such systems include an electrical heater (in the form of a high resistance wire) positioned within the probe shaft of each cryoprobe to thaw tissue after freezing to facilitate removal of the cryoprobe.

Some such cryosurgical systems may use Magnetic-Resonance Imaging for imaging a patient, for instance to guide the cryoprobes during insertion and/or to obtain images of anatomical features (e.g., tissue, tumor, and the like). An example of such systems can be found in U.S. Pat. No. 7,850,682, the disclosure of which is hereby incorporated by reference. Such systems may be desirable in situations where other imaging systems (such as Computed Tomography) may not be suitable (for instance, if exposure to radiation is not desired).

As a result of positioning several components of the surgical system outside the MRI magnet room, the surgical system may not be able to determine whether the MRI system is operational, as MR systems do not necessarily provide a standardized output that can be read by components of different types of surgical systems. Further, in some such systems, placement of surgical system having metallic and/or electrical components (e.g., probe shaft or heater wire and so on) adjacent to a MRI system may result in heating due to radiofrequency fields (radiofrequency heating), or induced current flow therethrough caused by the presence of the MRI magnet. Fault detection circuitry is a necessary mitigation to component failure. Fault detection circuits often have high input impedances which make them vulnerable to corruption when subjected to the high amplitude gradient and RF fields used by the MR scanner. Since these circuits interact directly with the probes, there is no way to shield them from the high amplitude fields. The ability to selectively disconnect and blank these circuits only while the MR scanner is operating has a significant advantage over systems that are unable to utilize these interfaces due to the potential for corruption.

SUMMARY

In an aspect, this disclosure provides a magnetic resonance imaging (MRI) guided cryosurgical system, operable in conjunction with a magnetic resonance (MR) system positioned in an MR room configured to produce MR signals, such as magnetic fields and radiofrequency signals. The magnetic and radiofrequency fields permit imaging of a region of patient tissue. The cryosurgical system includes elements, that can be physically separate from the MR system, at least portions of which are positionable in the MR room. The cryosurgical system can include one or more surgical tools at least portions of which are positionable inside the patient during surgery. At least one of the surgical tools may have one or more components that develop reactive effects (e.g. RF heating or unwanted induced currents) when exposed to MR signals generated by the MR system. The system includes a control system operatively connected to the surgical system that is configured to determine whether the MR system is in operation (for example by using), and if the control system determines that the MR system is in operation, mitigate the reactive effects of MR signals on components of the surgical tools, whereby mitigation comprises a reduction in the reactive effects induced in components of the surgical system.

In another aspect, this disclosure provides a magnetic resonance imaging (MRI) guided cryoablation system operable in conjunction with a magnetic resonance (MR) system according to any of the embodiments disclosed herein. The MR system may be positioned in an MR room. The system can include a cryoablation system positionable in the MR room. The cryoablation system can include a cryoprobe, at least a portion of which is positionable inside the patient tissue. The cryoprobe can have a probe shaft, having a distal section positionable in the patient tissue. The cryoprobe can comprise, particularly in the distal portion thereof, at least one of a) a probe shaft comprising metallic material; b) an electric heater, which may be configured to receive current and thereby heat the probe shaft so as to heat and/or thaw the patient tissue and electrical circuitry. The system can include one or more detectors positioned proximal to the MR system and configured to detect MR signals (such as RF and magnetic fields). The system can include a control system operatively connected to the cryoablation system. The control system can receive indication from the one or more detectors and determine whether the MR system is operational based at least on the indication received from the one or more detectors. If the control system determines that the MR system is operational, the control system can: if the cryoprobe has a probe shaft comprising metallic material, then initiate a cooling operation of the probe shaft, whereby the cooling operation comprises supplying a cooling; if the cryoprobe comprises an electrical heater, electrically disconnect the heater and/or ignore at least portions of electrical signals generated by the electric heater in response to exposure to MR signals; if the cryoprobe comprises electrical circuitry (for example electronic chip(s), fault detection and probe identification circuitry as described further herein) then disconnect and/or ignore electrical signals from the electrical circuitry. If the cryoprobe comprises one or more temperature sensors, then the control system may also be configured to disconnect and/or ignore electrical signals from the one or more of the temperature sensors.

In a further aspect, this disclosure provides a cryoablation system according to any of the embodiments disclosed herein. The cryoablation system can include a cryoprobe, having a probe shaft comprising a distal section insertable into a patient tissue and a cryofluid supply positioned within the probe shaft. The cryofluid supply can receive cryofluid, and supply a cryofluid toward the distal section of the probe shaft for cooling and/or freezing tissue. The cryofluid can be at cryogenic temperatures when supplied at a first pressure. The cryoablation system can include a low pressure cooling fluid source configured to supply a cooling fluid at a second pressure toward the distal section through the cryofluid supply. The second pressure can be less than the first pressure. The low pressure cooling fluid source configured to supply the cooling fluid so as to cool the distal section of the cryoprobe when a temperature of a portion of, or a component of the distal section of the cryoprobe exceeds a predefined threshold, or following detection of an MRI system in operation, such as by detecting magnetic resonance (MR) signals whereby cooling provided by the cooling fluid counteracts radiofrequency heating associated with the MRI system.

In a still further aspect this disclosure provides a cryoablation system, comprising a cryoprobe that has a probe shaft having a distal section insertable into a patient tissue; the cryoprobe may have a cryofluid supply within the probe shaft, the cryofluid supply being configured to receive cryofluid from a cryofluid source, and to supply the cryofluid toward the distal section of the cryoprobe for cooling the cryoprobe. The system may additionally comprise at least one cryofluid source that is configured to deliver cryofluid to the cryofluid supply. The system additionally comprises one or more sensors for detecting MR signals, or for measuring the temperature of the cryoprobe or one or more of the cryoprobes components. These sensors are typically selected from an RF sensor, a Magnetic field detector and one or more temperature sensors; the temperature sensors are typically configured to detect a rise in the temperature of a portion of, or a component of, the cryoprobe. The cryoablation system also comprises a control system which is operatively coupled to the one or more sensors such as to detect the presence of an RF signal or magnetic field or a rise in the temperature of the cryoprobe or a portion or component thereof that exceeds a predefined threshold. The control system may be additionally configured to control the supply of the cryofluid to the cryofluid supply and to deliver cryofluid to the cryofluid supply such as to cool the cryoprobe or a portion or component thereof upon detection of an MR signal, such as an RF signal or magnetic field, characteristic of an MRI system in operation; or a rise in temperature of the cryoprobe or a portion or component thereof that exceeding a predefined threshold.

In a still further aspect, this disclosure provides a cryoablation system, having a cryoprobe that comprises a probe shaft having a distal section insertable in a patient tissue, a cryofluid supply within the probe shaft, the cryofluid supply being configured to receive cryofluid from a cryofluid source, and to supply the cryofluid toward the distal section of the cryoprobe for cooling the cryoprobe. The cryoprobe may additionally comprise one or more electrical components. The system has at least one cryofluid source configured to deliver cryofluid to the cryofluid supply and one or more sensors suitable for detecting MR signals. These sensors are typically selected from an RF sensor and a Magnetic field detector. The system additionally comprises a control system operatively coupled to the one or more sensors suitable for detecting MR signals sensors such as to detect the presence of an operative MRI system, such as by detecting radiofrequency signals or magnetic fields characteristic of an MRI system in operation. The control system may be additionally configured to control the electrical supply to the one or more electrical components, and to electrically disconnect or isolate one or more of the electrical components upon detection of an RF signal or magnetic field characteristic of an MRI system in operation. Additionally, or alternatively, the control system may be configured to either ignore signals or readings from one or more of the electrical components or to accept or process only signals not affected by RF or magnetic fields upon detection of an RF signal or magnetic field characteristic of an MRI system in operation.

Certain aspects of the present disclosure include the following numbered embodiments:

1. A magnetic resonance imaging (MRI) guided surgical system,
   operable in conjunction with a magnetic resonance (MR) system positioned in an MR room, the MR system configured to produce MR signals, the MRI-guided surgical system comprising:
   a surgical system, at least portions of the surgical system being positionable in the MR room, the surgical system comprising one or more surgical tools at least portions of which are positionable inside a patient during surgery,
   at least one surgical tool having one or more components that develop reactive effects when exposed to MR signals generated by the MR system;
   a control system operatively connected to the surgical system, the control system being configured to:
      determine whether the MR system is in operation, and
      if the control system determines that the MR system is in operation, mitigate the reactive effects of MR signals generated by the MR system on components of the surgical tool, whereby mitigation comprises a reduction in the reactive effects induced in components of the surgical system.
2. The MRI-guided surgical system of embodiment 1, wherein at least one of the surgical tools comprises electrical components.
3. The MRI-guided surgical system of embodiment 1 or 2, wherein the control system is configured to electrically disconnect the electrical components if the control system determines that the MR system is generating MR signals.
4. The MRI-guided surgical system of embodiment 2 or any previous embodiment, wherein the control system is configured to ignore reactive electrical signals associated with the electrical components when exposed to MR signals if the control system determines that the MR system is generating MR signals.
5. The MRI-guided surgical system of embodiment 1 or any previous embodiment, wherein at least one of the surgical tools comprises metallic components.
6. The MRI-guided surgical system of embodiment 5 or any previous embodiment, wherein the control system is configured to determine whether the metallic components of the surgical system are heated by MR signals generated, and the control system is further configured to initiate a cooling operation to cool metallic components of the surgical system if the control system determines that the metallic components are heated by the MR signals.
7. The magnetic resonance imaging (MRI) guided surgical system of embodiment 1 or any previous embodiment, further comprising at least one of a radiofrequency (RF) sensor and/or at least one magnetic field detector, the at least one radiofrequency sensor and the at least one magnetic field detector being positionable so as to detect radiofrequency or magnetic field respectively when the MRI system is operational.
8. The magnetic resonance imaging (MRI) guided surgical system of embodiment 7 or any previous embodiment, wherein the control system is operatively coupled to the least one RF sensor and/or magnetic field detector and determines whether the MR system is generating MR signals based on radiofrequency signals sensed by the RF sensor and/or the magnetic field detected by the magnetic field detector.

9. The magnetic resonance imaging (MRI) guided surgical system of embodiment 1 or any previous embodiment, wherein the surgical system is physically separate from the MR system.

10. A cryoablation system, comprising:
a cryoprobe comprising:
a probe shaft having a distal section insertable into a patient tissue,
a cryofluid supply within the probe shaft, the cryofluid supply being configured to receive cryofluid, and to supply the cryofluid toward a distal section for cooling and/or freezing the patient tissue,
the cryofluid being at cryogenic temperatures when supplied in the cryofluid supply at a first pressure;
a low pressure cooling fluid source configured to supply a cooling fluid at a second pressure toward the distal section through the cryofluid supply, the second pressure being less than the first pressure,
the low pressure cooling fluid source being configured to supply the cooling fluid so as to cool the distal section of the cryoprobe when a temperature of a portion of the distal section or a component of the cryoprobe exceeds a predefined threshold, or following detection of a magnetic resonance imaging (MRI) system in operation, whereby cooling provided by the cooling fluid counteracts radiofrequency heating associated with the MRI system.

11. The cryoablation system of embodiment 10 or any previous embodiment, further comprising:
one or more detectors positioned proximal to the MR system and configured to detect MR signals; and
a control system operatively connected to the one or more detectors, the control system being configured to control the supply of the low pressure cooling fluid to the distal section of the cryoprobe in response to the detection of MR signals.

12. The cryoablation system of embodiment 11 or any previous embodiment, further comprising a temperature sensor for measuring the temperature of the distal section of the cryoprobe, the temperature sensor being operatively coupled to the control system, the control system is configured to supply the low pressure cooling fluid in response to receiving the temperature measured by the temperature sensor.

13. The cryoablation system of embodiment 11 or any previous embodiment, wherein the control system is operatively coupled to the low pressure cooling fluid source, the control system being configured to:
communicate with the temperature sensor to initiate a temperature measurement of the distal section;
receive measured temperature from the temperature sensor;
determine whether the temperature exceeds the predefined threshold; and
communicate with the low pressure cooling fluid source to initiate supply of the cooling fluid.

14. The cryoablation system of embodiment 13 or any previous embodiment, wherein the temperature sensor is further configured to measure the temperature of the distal section when the cooling fluid is supplied by the low pressure cooling fluid source.

15. The cryoablation system of embodiment 10 or any previous embodiment, wherein a magnetic resonance (MR) imaging system is positioned in an MR room, the MR signals being associated with the MRI system, the cryoablation system being positionable in the MR room and operational in conjunction with the MRI system.

16. The cryoablation system of embodiment 11 or any previous embodiment, wherein the control system is configured to determine a duration over which the cooling fluid from the low pressure cooling fluid source is to be supplied, the duration corresponding to time intervals over which the temperature of the distal section exceeds the predefined threshold, and/or time intervals over which the MRI system generates MR signals.

17. The cryoablation system of embodiment 11 or any previous embodiment, wherein the control system is configured to initiate supply of the cooling fluid during insertion of the cryoprobe into the patient tissue.

18. The cryoablation system of embodiment 12 or any previous embodiment, wherein the control system is configured to determine a first quantity of heat to be removed from the distal section of the probe shaft, the first quantity of heat corresponding to measured temperature increase over the predefined threshold, the control system being further configured to determine a first flow rate of the cooling fluid required to remove the first quantity of heat from the distal section.

19. The cryoablation system of embodiment 18 or any previous embodiment, wherein the control system is configured to predict an increase in temperature over the predefined threshold when the cryoprobe is inserted into the patient and/or when MR signals are detected, and configured to determine a second quantity of heat to be removed from the distal section of the probe shaft, the second quantity of heat corresponding to the predicted increase in temperature over the predefined threshold, the control system being further configured to determine a second flow rate of the cooling fluid required to remove the second quantity of heat from the distal section.

20. The cryoablation system of embodiment 10 or any previous embodiment, wherein the cooling fluid is argon.

21. The cryoablation system of embodiment 10 or any previous embodiment, wherein the second pressure is less than about 500 psi.

22. The cryoablation system of embodiment 20 or any previous embodiment, wherein the cooling fluid is supplied over a duration so as to result in a temperature drop of the distal section between about 2° C. and about 8° C.

23. The cryoablation system of embodiment 10 or any previous embodiment, wherein the cryofluid is the same fluid as the cooling fluid.

24. A magnetic resonance imaging (MRI) guided cryoablation system
operable in conjunction with a magnetic resonance (MR) system positionable in an MR room, the MR system configured to produce MR signals, the MRI-guided surgical system comprising:
a cryoablation system positionable in the MR room, the cryoablation system comprising:
a cryoprobe at least a portion of which being positionable inside the patient tissue, the cryoprobe comprising
a probe shaft having a distal section positionable in the region of the patient tissue, the cryoprobe comprising at least one of the following:
a. a probe shaft comprising metallic material,
b. an electric heater configured to receive current and thereby heat the probe shaft so as to heat and/or thaw the patient tissue,
c. electrical circuitry,
one or more detectors positioned proximal to the MR system and configured to detect MR signals; and
a control system operatively connected to the cryoablation system and being configured to:
receive indication from the one or more detectors,
determine whether the MR system is operational based at least on the indication received from the one or more detectors, and
if the control system determines that the MR system is operational:
if the cryoprobe comprises a probe shaft comprising metallic material, then initiate a cooling operation of the probe shaft, whereby the cooling operation comprises supplying a cooling fluid,
if the cryoprobe comprises an electrical heater, electrically disconnect the heater and/or ignore at least portions of electrical signals generated by the electric heater in response to exposure to MR signals,
if the cryoprobe comprises electrical circuitry then disconnect and/or ignore electrical signals from the electrical circuitry.

25. The cryoablation system of embodiment 24 or any previous embodiment, wherein the electrical circuitry comprises an electronic chip.

26. A cryoablation system, comprising:
a cryoprobe comprising:
a probe shaft having a distal section insertable into a patient tissue,
a cryofluid supply within the probe shaft, the cryofluid supply being configured to receive cryofluid from a cryofluid source, and to supply the cryofluid toward the distal section of the cryoprobe for cooling the cryoprobe
at least one cryofluid source configured to deliver cryofluid to the cryofluid supply
One or more sensors selected from an RF sensor, a Magnetic field detector and a temperature sensor; the temperature sensor configured to detect a rise in the temperature of a portion of or a component of the cryoprobe;
and a control system operatively coupled to the one or more sensors such as to detect the presence of an RF signal or magnetic field or a rise in the temperature of the cryoprobe or a portion or component thereof exceeding a predefined threshold,
the control system additionally configured to control the supply of the cryofluid to the cryofluid supply and to deliver cryofluid to the cryofluid supply such as to cool the cryoprobe or a portion or component thereof upon detection of either
an RF signal or magnetic field characteristic of an MRI system in operation; or
a rise in temperature of the cryoprobe or a portion or component thereof exceeding a predefined threshold.

27. A cryoablation system according to embodiment 26 or any previous embodiment, wherein the cooling provided by the cryofluid counteracts radiofrequency heating associated with the Mill system.

28. A cryoablation system according to embodiment 26 or any previous embodiment, wherein the control system is configured to deliver cryofluid to the cryofluid supply at a cryogenic temperature for cooling and/or freezing a patients tissue and at a non-cryogenic temperature to cool the cryoprobe or a portion or component thereof upon detection of an RF signal or magnetic field characteristic of an MRI system in operation or of a rise in temperature of the cryoprobe or a portion or component thereof exceeding a predefined threshold.

29. A cryoablation system according to embodiment 26 or any previous embodiment, wherein the cryoprobe comprises one or more of an electrical heater, a temperature sensor and an electronic chip and the control system is configured to electrically disconnect or isolate the electrical heater, temperature sensor or electronic chip upon detection of an RF signal or magnetic field characteristic of an MRI system in operation.

30. A cryoablation system, comprising:
a cryoprobe comprising:
a probe shaft having a distal section insertable into a patient tissue,
a cryofluid supply within the probe shaft, the cryofluid supply being configured to receive cryofluid from a cryofluid source, and to supply the cryofluid toward the distal section of the cryoprobe for cooling the cryoprobe; the cryoprobe additionally comprising one or more electrical components;
at least one cryofluid source configured to deliver cryofluid to the cryofluid supply;
one or more sensors selected from an RF sensor and a magnetic field detector; and
a control system operatively coupled to the one or more sensors such as to detect the presence of an RF signal or magnetic field;
wherein the control system is additionally configured to control the electrical supply to the one or more electrical components, and to electrically disconnect or isolate one or more of the electrical components; and/or
wherein the control system is additionally configured to either ignore signals or readings from one or more of the electrical components or to accept or process only signals not affected by RF or magnetic fields;
upon detection of an RF signal or magnetic field characteristic of an MRI system in operation.

31. A cryoablation system according to embodiment 30 or any previous embodiment, wherein the one or more electrical components are selected from electrical heaters, temperature sensors, and electronic chips.

32. A cryoablation system according to embodiment 31 or any previous embodiment, wherein the controller is configured to electrically disconnect or isolate one or more of an electrical heater, a temperature sensor, and an electronic chip.

33. A cryoablation system according to embodiment 31 or any previous embodiment, wherein the controller is configured to ignore signals or readings that correspond to faults in an electrical heater.

34. A cryoablation system according to embodiment 31 or any previous embodiment, wherein the controller is configured to ignore signals or readings from an electrical heater except those that correspond to electrical resistance of the heater.

35. A cryoablation system according to embodiment 32 or any previous embodiment, wherein the controller is configured to ignore signals or readings from a temperature sensor except those that correspond to electrical resistance of the temperature sensor.

36. A cryoablation system according to embodiment 34 or any previous embodiment, wherein the temperature of the electrical heater is determined from its electrical resistance.

37. A cryoablation system according to embodiment 35 or any previous embodiment, wherein the temperature of the cryoprobe or one of its components is determined by the electrical resistance of one or more temperature sensors.

The details of one or more examples are set forth in the accompanying drawings and the description below. Other features, objects, and advantages will be apparent from the description and drawings, and from the claims.

BRIEF DESCRIPTION OF DRAWINGS

FIG. 2 is a front view of a cryoprobe connectable to the control system of FIG. 2 according to a non-limiting exemplary embodiment;

FIG. 3 is a sectional front view of the cryoprobe of FIG. 2;

FIG. 4 is a schematic illustrating a method of operating a surgical system in conjunction with a MRI system according to a non-limiting exemplary embodiment;

FIG. 9 is an electrical schematic for electrically disconnecting portions of a surgical tool according to a non-limiting exemplary embodiment.

DETAILED DESCRIPTION

Cryosurgical systems can be used for cryoablating target tissues (e.g., a tumor). Typically, such systems include one or more cryoprobes, one or more cryofluid sources and a control system. The cryofluid sources can supply gases such as argon, nitrogen, air, krypton, $CO_2$, $CF_4$, xenon, and various other gases that are capable of reaching cryogenic temperatures (e.g., temperatures below 190 K) when expanded from pressures greater than about 1000 psi. As used herein, "cryofluid" can refer to any fluid that reaches low temperatures (e.g., below 190 Kelvin) when expanded from pressures greater than about 1000 psi (e.g., typically around 3500 psi). The cryosurgical system can also include a control system having one or more sensors, flow meters, timers, analog/digital converters, wired or wireless communication modules, etc. Additionally, the control system can also regulate the flow rate, temperature and pressure of cryofluid supplied to the cryoprobe.

During cryosurgery, for instance, a surgeon may deploy one or more cryoprobes to cryoablate a target area of a patient anatomy by placing the cryoprobe at or near the target area of the patient anatomy. In one example, cryoprobe utilizes the Joule-Thomson effect to produce cooling or heating. In such cases, a cryofluid expands in the cryoprobe from a higher pressure to a lower pressure. Expansion of the cryofluid results in temperatures at or below those necessary for cryoablating a tissue in the vicinity of the tip of the cryoprobe. Heat transfer between the expanded cryofluid and the outer walls of the cryoprobe can be used to form an iceball, and consequently cryoablate the tissue.

Figure 1:
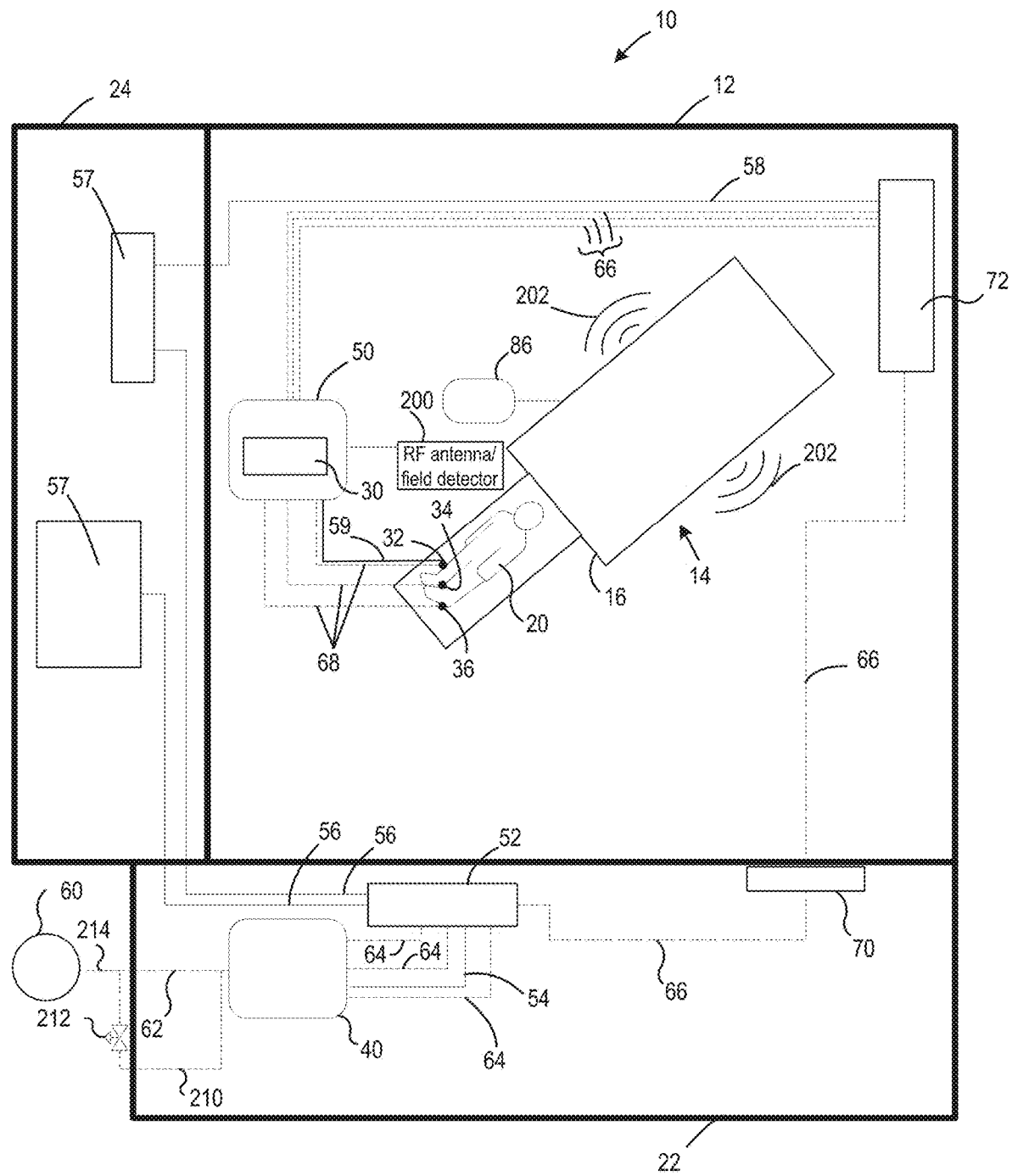
FIG. 1 is a schematic of a Magnetic Resonance Imaging (hereinafter "MRI")-guided cryosurgery system according to a non-limiting exemplary embodiment.

FIG. 1 is a schematic of a Magnetic Resonance Imaging (hereinafter "MRI")-guided cryosurgery system 10 according to a non-limiting exemplary embodiment. The system of FIG. 1 can include components of a MRI system positioned inside a magnet room 12. The MRI system comprises a MRI scanner 14 having a MRI magnet 16 having a bore for accommodating a patient 20. The MRI magnet 16 can be of open or closed type, and can include access ports to allow a surgeon to access the patient 20. The MRI magnet 16 can also have electrical connection lines (illustrated by solid lines) and/or mechanical or fluid connection lines (illustrated by dashed lines) in FIG. 1 for connecting to various electrical, control and/or cryoablation systems as will be described further below. The system can also include a control room 22 electrically isolated from the magnet room 12, and an equipment room 24. The MRI system may image the patient before insertion of surgical tools 32, 34, 36 to visualize patient areas of interest, such as a tumor or a patient cavity. Further, imaging may be performed during insertion to guide the surgical tool to the intended location inside the patient. Additionally, imaging may be performed after insertion and during surgery, as well as after surgery.

Continuing with FIG. 1, in a non-limiting exemplary embodiment, the connection lines may terminate in one or more surgical tools 32, 34, 36, such as cryoprobes insertable inside a patient 20. Accordingly, in some such examples, the system may include a connector interface 30 placed inside the magnet room 12 for permitting connection of one or more surgical tools 32, 34, 36, 34, 36 to other components of the surgical systems (e.g., cryoablation systems) that may be placed outside the magnet room 12 (for instance, in a control room 22 or an equipment room 24). For instance, the system may include electrical connection lines 54 and fluid connection lines 62 extending from the control room 22 to the magnet room 12, so as to operatively connect a control system 40 to the surgical tools 32, 34, 36. The connector interface 30 can, in some advantageous embodiments, be provided on a mobile cart 50 positioned proximal to the magnet to permit a plurality of surgical tools 32, 34, 36 to be directly or indirectly (e.g., electrically and/or fluidly) connected to the control system 40 positioned outside the magnet room 12 (e.g., in the control room 22). The control system 40 can, in some advantageous embodiments be a programmable microprocessor that can read computer-readable instructions (e.g., in the form of a software program and execute one or more operations, as will be detailed below).

The electrical and fluid connections between the control system 40 and the surgical tools 32, 34, 36 will be described according to an example embodiment. The control system 40 can be electrically connected to a junction box 52 located external to the magnet room 12 by way of a first set of electrical connection lines 54. Further, the junction box 52 can include a second set of electrical connection lines 56 to connect to electrical and/or imaging equipment 57 (such as an imaging router and electrical filters) located external to the magnet room 12 (for instance, within the equipment room 24). A third set of electrical connection lines 58 may connect the electrical and/or imaging equipment 57 to the connector interface 30 and/or mobile cart 50 located inside the magnet room 12. The junction box 52 can permit removable electrical connection between components in the magnet room 12 and components in the electrical and/or control rooms.

Referring again to FIG. 1, in some examples, the system may be used to perform many types of surgical procedures, and the systems and methods disclosed herein should not be construed as limiting to any one type of surgical procedure, such as cryosurgical procedures.

In certain examples, the surgical system can be a cryosurgery system, such as a cryoablation system. Accordingly in some examples, the system may include one or more cryofluid sources 60. The cryofluid source can be a liquid or gas container.

Cryofluid may be delivered at cryogenic temperatures and pressures to surgical tools 32, 34, 36 (e.g., cryoprobes). The cryofluid source can be a cooling gas such as argon, nitrogen, air, krypton, $CF_4$ xenon, or $N_2O$.

The control system may be configured to deliver cryofluid to a cryoprobe at cryogenic temperature for cooling and/or freezing a patients tissue and at a non-cryogenic temperature to cool the cryoprobe or a portion or component thereof, such as upon detection of an RF signal or magnetic field characteristic of an MRI system in operation, or upon detection of a rise in temperature of the cryoprobe or a portion or component thereof exceeding a predefined threshold. In some cryoprobes the cryofluid can be delivered to the cryofluid supply as described elsewhere herein.

As exemplified in FIG. 1, in some approaches, the cryofluid source is positioned outside the magnet room 12 and is fluidly connectable to the control system 40 by way of a first set of fluid connection lines 62. The control system 40 in turn can be fluidly connected to the connector interface 30 and/or mobile cart 50 by way of a second set of fluid connection lines 64 and a third set of fluid connection lines 66. A fourth set of fluid connection lines 68 can fluidly connect the surgical tools 32, 34, 36 (e.g., cryoprobes) to the connector interface 30 and/or mobile cart 50. The fluid lines can be flexible and/or detachable and may include other fluid components to regulate pressure of fluid passing therethrough. Fluid from the cryofluid source may thus be conveyed by the set of fluid connection lines 62, 64, 66 and 68 to the surgical tools 32, 34, 36. Optionally, the system can include a fluid connection panel 70 electrically isolated from the magnet room 12 so as to permit fluid connections between components present in the magnet room 12 and those in the control room 22. Similarly, an electrical connection panel 72 can facilitate electrical connections between components present in the magnet room 12 and those in the control room 22 and/or electrical room.

Referring back to FIG. 1, a system may also include an MRI display 86 operatively coupled to the MRI scanner 14 and positioned within the magnet room 12 for displaying an image representative of an anatomical feature of a patient 20 so as to provide guidance to a surgeon during surgery. The MRI display 86 can be operatively coupled to electrical and/or imaging components in the equipment room 24 and the control system 40 located within the control room 22. Such a configuration may display information relating to the operating conditions of the overall system. In such cases, advantageously, the MRI display 86 may enable a surgeon to select a desired image, for example, to monitor the progress of the surgical process, images relating to MRI guidance and/or current information relating to one or more surgical tools 32, 34, 36. Optionally, more than one display may be provided in the magnet room 12 to permit simultaneous visualization of various aspects of the surgical procedure.

As described earlier, a surgical tool can be a cryoprobe 100 in a non-limiting exemplary embodiment. FIG. 2 is a front view of one such cryoprobe 100 and FIG. 3 is a sectional front view of the cryoprobe 100 of FIG. 2. Referring to FIGS. 2 and 3, the cryoprobe 100 can include an elongate body. Components of the cryoprobe 100 can be located within a probe shaft 102. The cryoprobe can, in some cases, be a cryoneedle. The probe shaft 102 can terminate in a distal operating tip 104 disposed at a distal section 106 of the cryoprobe 100 for penetrating through tissues of a patient 20 during deployment. In embodiments where the cryoprobe is configured as a cryoneedle, the distal operating tip 104 can penetrate the patient's skin. In alternate embodiments, the cryoprobe can be a flexible probe, and may be inserted by way of a catheter. A proximal coupler 108 can facilitate connections of the cryoprobe 100 to a connector interface 30, control system 40 and/or cryofluid source.

The probe shaft 102 can be of substantially thin cross section to allow deployment in tissues of a patient 20. In an example, the cryoprobe can be a cryoneedle, having a probe shaft 102 outer diameter of about 2.1 millimeters. Other dimensions of the probe shaft 102 are also contemplated. For example, the probe shaft 102 can have an outer diameter of between about 1.5 millimeters and about 2.4 millimeters. In addition, in embodiments where the cryoprobe is a cryoneedle, the distal operating tip 104 can be made of a pliant material so as to be flexible (e.g., relative to the proximal portion of the cryoprobe 100) for penetrating soft tissue. Alternatively, a substantial portion of the cryoprobe can be generally flexible and may not pierce the patient skin, and may be flexible (bendable) about its central axis, by a desired angle.

As seen in FIG. 3, the cryoprobe 100 includes a cryofluid supply 112 extending substantially along its length for providing a high-pressure cryofluid to the distal operating tip 104. The cryofluid supply 112 can be positioned coaxially/concentrically within the probe shaft 102. The cryofluid supply 112 can be configured to supply a cryofluid for forming iceballs on an outer surface of the probe shaft 102 over the distal section 106. In some cases, the cryofluid supply 112 can be a capillary tube.

With continued reference to FIG. 3, in some examples, the cryoprobe 100 includes a cryocooler. For instance, in the illustrated example, the cryofluid supply 112 can terminate in a Joule-Thomson orifice 114. The Joule-Thomson orifice 114 can be positioned near the distal operating tip 104, so as to permit cryofluid exiting the Joule-Thomson orifice 114 to expand into an expansion chamber. Accordingly, a high-pressure cryofluid supplied via the cryofluid supply 112 exits through the Joule-Thomson orifice 114 and expands in the expansion chamber. As the cryofluid expands in the expansion chamber, it cools rapidly and forms iceballs of different shapes and/or sizes over the outer surface of the distal operating tip 104. The expansion of the cryofluid can be such that when expanded, the cryofluid is colder than the incoming cryofluid. While an exemplary cryocooler such as a Joule-Thomson orifice 114 is illustrated, it should be understood that other types of cryocoolers such as cryogenic dewars, Stirling-type cooler, pulse-tube refrigerator (PTR), Gifford-McMahon (GM) cooler, and the like are contemplated within the scope of the present disclosure. Further, as briefly noted above, cryofluids which may be used for cooling include argon, liquid nitrogen, air, krypton, $CF_4$, xenon, or $N_2O$.

Referring again to FIG. 3 for illustrative purposes, in some examples, a heater 116 can optionally be provided within the probe shaft 102 to facilitate thawing and/or cauterizing tissue. In some such examples, the heater 116 may be operated after cooling and iceball formation to thaw frozen tissue to facilitate disengagement of cryoprobe 100 therefrom. As illustrated in this exemplary embodiment, an electrical heater 116 can be provided coaxially with the cryofluid supply 112 and the probe shaft 102 to facilitate heating the distal section 106 of the cryoprobe 100. Alternatively, the electrical heater 116 can be positioned elsewhere in cryoprobe 100 to heat the distal section 106 of the cryoprobe 100. The electrical heater 116 can be a resistive heater 116 and can include a helically-wound electrical wire which can generate heat proportional to the current flow therethrough and the electrical resistance of electrical heater 116. In such cases, as alluded to previously, the control system 40 (shown in FIG. 2) can supply and/or regulate electrical current flow to the electrical heater 116 within the cryoprobe 100.

In some systems, the control system comprises one or more temperature sensors configured to measure the temperature of the surgical tool or a component thereof. For instance, the control system can include a temperature sensor for measuring temperature of the distal section 106 of the cryoprobe 100, or of the cryoprobe shaft or of an electronic chip or of an electrical heater. Temperature measurement may be performed before, during or after placement inside the patient to monitor probe temperature or the temperature of any of its components, for example measurement may occur during placement and/or during a surgical procedure (e.g., thaw or cautery procedure) or before the procedure, whilst the system is being set up or prepared for use. In an example, the temperature sensor can comprise resistive materials whose electrical resistance may change when temperature thereof changes (e.g., a positive temperature coefficient material). The change in resistance can be measured by the control system 40, and consequently, the temperature change be determined by the control system 40 based on known correlations between resistance and temperature for the specific type of material. Likewise, the temperature of the electrical heater may also be determined in this manner.

As described above, the cryoprobe 100 comprises electrical heater 116. Accordingly, in certain advantageous embodiments the materials of the electrical heater 116 (such as the heater 116 wire) can perform dual functions of resistively heating the probe shaft 102 when current flows therethrough, and providing temperature feedback to the control system 40 during probe heating. Electrical heaters may also be provided with a needle heating element fault detection circuitry. Such circuitry may be operatively connected to the control system for the purposes of fault detection. The control system may be configured to "blank" or ignore signals from this fault detection circuitry in the presence of an operative MRI system as described further herein.

In some advantageous examples, referring back to FIG. 1, the surgical tools 32, 34, 36 may include electronic components that permit identification thereof when connected to the connector interface 30 and/or mobile cart 50. In an example, the surgical tool is a cryoprobe 100 as illustrated in FIGS. 2 and 3. the surgical tool 100 may include an electronic chip 120. The chip is advantageously positioned in the proximal portion (e.g., near the proximal connector) In other examples, the surgical tool can include an electronic chip 120 anywhere along its body. The electronic chip 120 can include a non-transitory data storage medium that can be machine readable. Electrical connections between the connector interface 30 and/or mobile cart 50, and the control system 40 may permit the control system 40 to have read/write access of the electronic chip 120.

The electronic chip 120 can permit identification of the surgical tool when multiple surgical tools 32, 34, 36 are connected to the mobile cart 50. For example, each electronic chip 120 can store a unique surgical tool identifier in its memory, and may thereby permit identification of the surgical tool connected to a particular connector port on the connector interface 30. Additionally, the electronic chip 120 may store other information, such as the duration over which a particular surgical procedure was performed, the total amount of time during which the surgical tool was used, and the like. Further, such information may be transmitted (e.g., via electrical connections) to the control system 40.

As described previously with reference to FIG. 1, certain components of the surgical system are positionable proximate to MRI system or within the MR room, that permits imaging and guidance before, during or after surgery. When positioned in this way, components of the system are subject to MR signals when the MR system is operational, such as magnetic fields necessary for imaging a region of a patient's tissue, and radiofrequency emissions. For instance, the surgical tools 32, 34, 36 can be connected to the fourth set of electrical connection lines 59 from the mobile cart 50, in turn connected to the connector interface 30. In FIG. 1, one of the surgical tools is shown as being connected to the mobile cart 50 by way of connection line 59, however, substantially all the surgical tools may be connectable to the mobile cart 50 by way of individual connection lines 59 (e.g., as shown in FIG. 9). Returning to FIG. 1, surgical tools 32, 34, 36 may include components that are configured to develop reactive effects when exposed to magnetic resonance (MR) signals generated by the MRI system. For example, the metallic material of the probe shaft 102 may be heated when exposed to radiofrequency fields. Additionally, surgical tools 32, 34, 36 may include electrical components (e.g., heater 116 wire, temperature probes or electronic chips 120) that may permit induced current flow therethrough. Accordingly, certain embodiments of the present disclosure provide systems and methods for mitigating reactive effects introduced into components of the surgical system when exposed to MR signals 202. Such advantageous embodiments may permit use of the surgical tools 32, 34, 36 having metallic or electrical components in conjunction a MRI system, as will be described below.

In certain aspects of the present disclosure, the MRI system may be used simultaneously, or periodically at various points during a cryosurgical procedure. FIG. 4 illustrates one such non-limiting exemplary method 400 of MRI operation in conjunction with placement of a surgical tool within a patient. In such cases, the MRI scanner 14 may be operated at step 402 to generate an image so as to determine, at step 404 position of a surgical tool (e.g., cryoprobe 100) relative to the target area inside a patient (e.g., a tumor). If the surgeon and/or the control system 40 determine at step 406 that the surgical tool has not been placed at the intended target site, at step 408, the surgical tool may be advanced toward the intended target site. At step 410, a follow-up MRI scan may be performed to visualize the new position of the surgical tool relative to the target site. This process can be repeated until the surgical tool is placed at the target site. Appreciably, the steps in FIG. 4 do not constitute a sequence of execution, and the MRI scanner 14 operation and the advancement of the surgical tool may be simultaneous.

Figure 5:
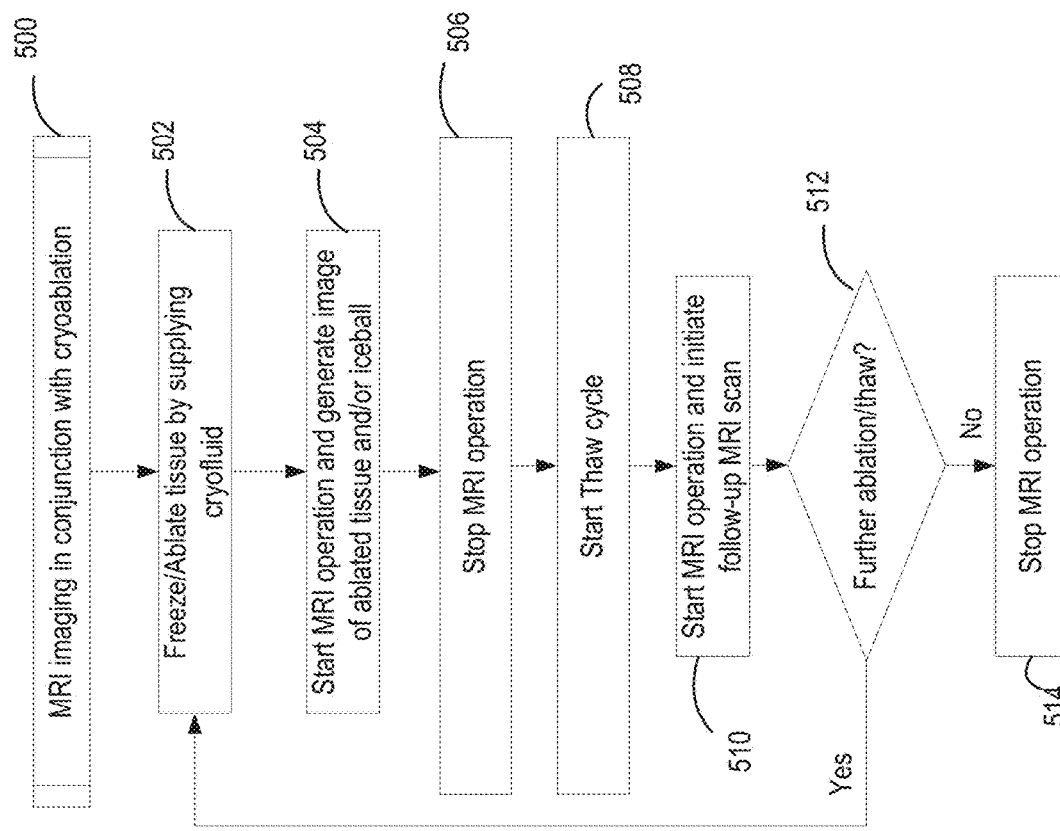
FIG. 5 is a schematic illustrating another method of operating a surgical system in conjunction with a MRI system according to a non-limiting exemplary embodiment.

FIG. 5 illustrates another non-limiting exemplary method 500 of operation of MRI system in conjunction with surgical system. In this operation, the surgical procedure can be a cryoablation procedure for ablating a tumor. Accordingly, at step 502, the control system 40 may initiate a "FREEZE" cycle, whereby a cryofluid is supplied to the surgical tool (e.g., cryoprobe 100) to form iceballs and ablate the tissue. At step 504, MRI scanner 14 may be operated to visualize the size of the iceball and/or other features of interest (e.g., position of surgical tool relative to tumor, etc.). At step 506, MRI scanner 14 operation may be stopped, and at step 508, a "THAW" cycle may be performed to thaw the tip of the surgical tool (e.g., cryoprobe 100) to facilitate removal thereof from the patient tissue. At step 510, MRI scanner 14 may be operated to visualize the ablated tumor, to permit the surgeon and/or control system 40 to determine if a subsequent "FREEZE" cycle is necessary, at step 512. This process may be repeated until a desired clinical result is achieved. Optionally, the MRI scanner 14 may continue operating throughout the procedure (e.g., during "FREEZE" as well as "THAW" cycles) until step 514, whereby the MRI operation is stopped. Alternatively, the MRI scanner 14 may be operated intermittently to obtain relevant information regarding the surgical procedure.

As seen from the above examples, it may be advantageous for the control system 40 to know the duration and start/stop times of MRI scanner 14 operation, so as to determine whether any mitigation due to MRI operation is to be performed. Accordingly, in some such exemplary embodiments, the control system 40 can be operatively connected to MR scanner detectors (for example antennas tuned to receive the low frequency gradient field and/or high frequency RF field emitted during normal use of MR equipment) 200 so as to determine whether the MRI scanner 14 is operational, and if so, the duration over which the MRI scanner 14 operates, and other necessary parameters. Such systems may advantageously be a smart/intelligent surgical system, as will be described below.

Referring back to FIG. 1, in some examples, the system may include at least one detector, for example one or more radiofrequency (RF) sensors and/or at least one magnetic field detector 200 positionable so as to detect radiofrequency or magnetic field respectively when the MRI system is operational. These detectors may be advantageously positioned proximate to the MR and configured to detect MR signals. The control system is advantageously operatively coupled to the detectors and determines whether the MR system is operational (for instance, generating MR signals) based on radiofrequency signals sensed by the RF sensor and/or the magnetic field detected by the magnetic field detector and is configured to take action to mitigate the effects of the MR signals on the surgical system, and cryoprobes or their components. Advantageously, the RF sensor and/or the magnetic field detector 200 may be positioned inside the magnet room 12, at a desirable distance from a bore of the MRI system so as to detect radiofrequency or magnetic field 202 respectively when the MRI system is imaging the portion of the patient. The RF sensor can be a RF antenna and/or a magnetic field sensor. In an example, the RF sensor and/or magnetic field sensor can be an off-the-shelf antenna tuned to (or otherwise responsive to) the frequency of MR signals associated with the MR scanner. The RF sensor and magnetic field detector 200 can have a dynamic range sufficient to permit them to be located anywhere in the magnet room 12, and still be able to detect RF signals and/or low frequency magnetic field 202 associated with MRI scanner 14. As is apparent, during MRI scanner operation, both radiofrequency signals as well as a magnetic field 202 can be generated by components of MR system (magnetic coils, radiofrequency transducers etc.) Accordingly, it is sufficient to include either a RF sensor or a field detector. Advantageously, certain non-limiting exemplary embodiments of the present disclosure include both a RF sensor and a magnetic field detector 200 to provide redundancy in detection of MR signals 202 (for instance, if one of the RF sensor or the field detector were to not detect scanner operation). Advantageously, the RF sensor and the field detector may not transmit or reradiate signals and may only be configured to receive signals from the MRI scanner 14. Such embodiments may therefore not introduce noise or artifacts in the image generated by the MRI system.

The RF sensor and/or field detector may be operatively coupled to the control system 40. For instance, the RF sensor and/or field detector may utilize existing electrical connections between the mobile cart 50 and the control system 40. In one such example, as illustrated, the RF sensor and/or field detector may be electrically coupled to the mobile cart 50 positioned in the magnet room 12. As described previously, the mobile cart 50 may in turn be electrically coupled to the control system 40, thereby having the RF sensor and/or field detector in electrical communication with the control system 40. Optionally, the RF sensor and/or field detector can be physically mounted within the mobile cart 50 so as to provide an efficiently-packaged system.

The RF sensor and/or field detector may detect MR signals 202 (e.g., RF or magnetic) when the MRI scanner 14 is being operated, and may generate an output signal. In some examples, the output signal may be an analog signal, and the system may include an A/D convertor to convert the analog signal into a digital signal. Alternatively, the output signal may be a digital signal. The output signal from RF sensor and/or the magnetic field detector 200 may be sent to the control system 40. In such cases, the control system 40 determines whether components of the MR system (such as the MRI scanner 14) are generating MR signals 202 based on RF signals sensed by the RF sensor and/or the magnetic field 202 detected by the magnetic field detector 200.

As mentioned previously, components of the surgical system may develop reactive effects when exposed to MR signals 202 generated by the MR system. For example, the surgical tools 32, 34, 36 (e.g., cryoprobes) may have metallic components, (for example probe shafts may comprise a metal, or the electrical heater or temperature probe may comprise a metal wire) and may undergo radiofrequency heating when exposed to RF signals. Depending on the strength of the RF signals, the temperature of the surgical tools, 32, 34, 36 portions of them or components of them may increase to unacceptable levels. This may, for example cause patient discomfort and/or necrosis of healthy tissue during placement of the surgical tool inside the patient. Accordingly, the control system 40 may be configured to mitigate reactive effects developed when portions or components of the surgical system are exposed to the MR signals 202.

The temperature of such systems and components can be monitored by the control system for example by the provision of temperature probes operatively coupled to the system and configured to report the temperature. Alternatively the temperature of electrical components may be determined by monitoring the resistance of electrical wires, whose resistance varies with temperature.

Figure 6:
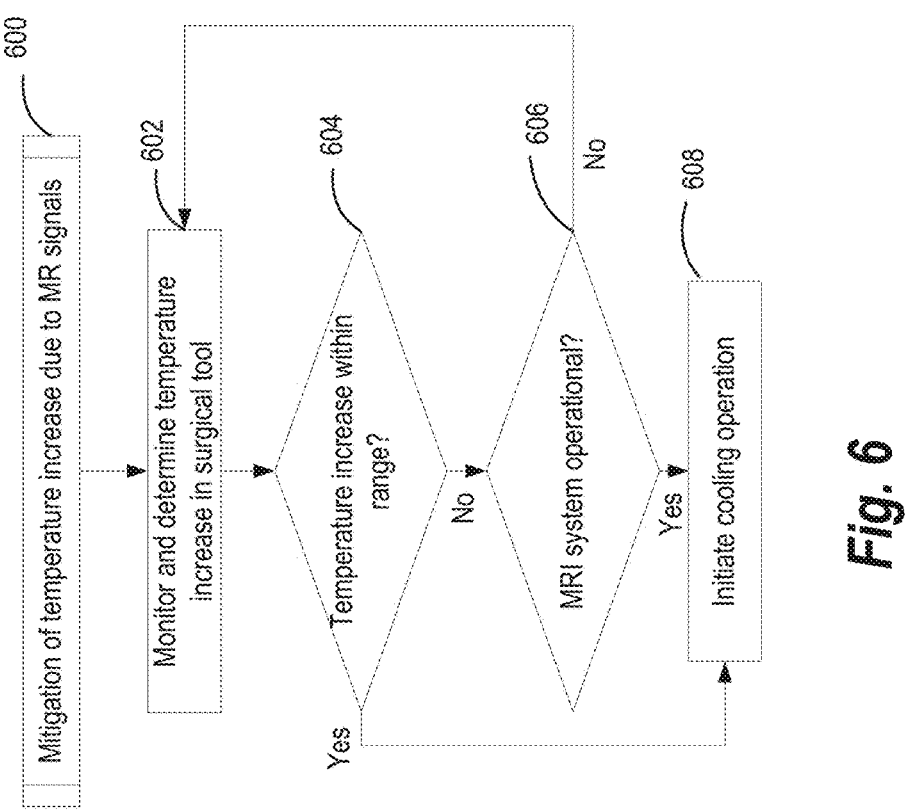
FIG. 6 is a schematic illustrating a mitigation procedure according to a non-limiting exemplary embodiment.
Figure 7:
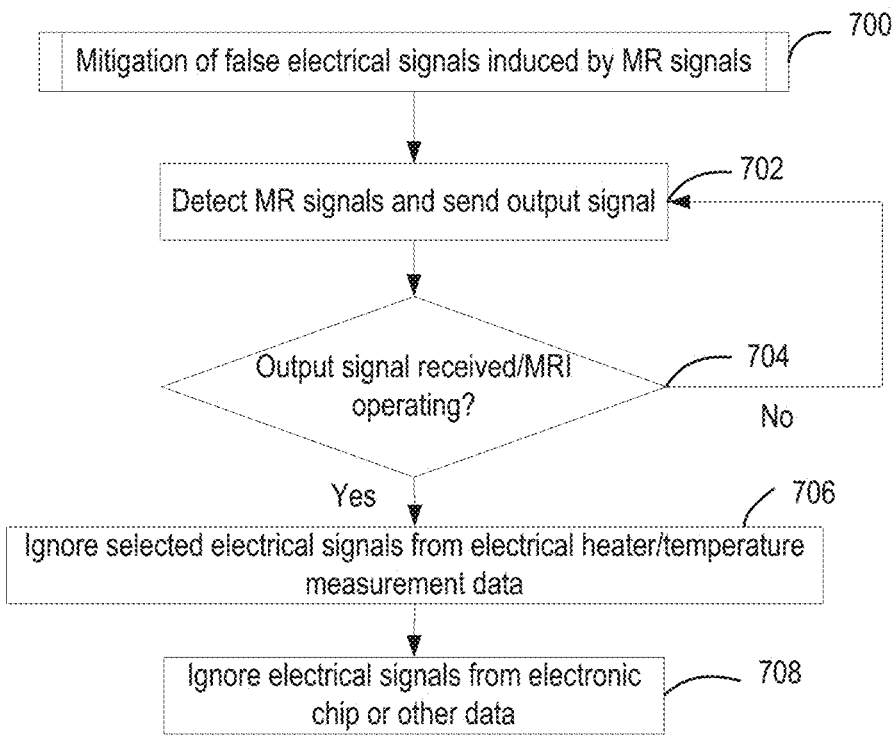
FIG. 7 is a schematic illustrating another mitigation procedure according to a non-limiting exemplary embodiment.
Figure 8:
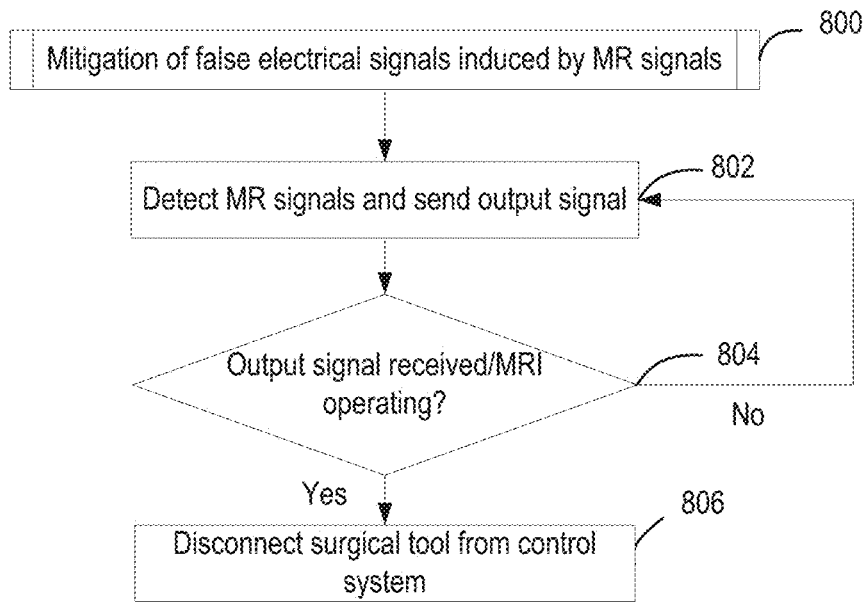
FIG. 8 is a schematic illustrating another mitigation procedure according to a non-limiting exemplary embodiment.

FIGS. 6, 7 and 8 illustrate various potential mitigation procedures 600, 700 and 800 that can be performed by the control system 40. Mitigation procedures 600, 700, and 800 can be performed in any sequence. Further, the mitigation procedures 600, 700, and 800 can be performed in conjunction with each other.

In a non-limiting exemplary embodiment, the control system 40 can determine whether MR signals 202 induce heating, such as radiofrequency heating in portions or components of surgical tools for example during placement thereof inside a patient, and initiate a cooling operation (for example using cryofluid) to cool the portion or component, for example if the temperature exceeds a predetermined threshold temperature, or upon detection of magnetic resonance (MR) signals. FIG. 6 illustrates an example of such a mitigation procedure 600. In this example, mitigation comprises reduction of temperature of the surgical tool, a portion thereof or a component thereof. With reference to FIGS. 1 and 6, in step 602, the control system 40 may determine the temperature increase of the surgical tools 32, 34, 36, such as a cryoprobe, or a part of it, for example of the distal portion, or a component thereof, such as the probe shaft. The control system 40 may determine whether the temperature increase exceeds a predefined threshold at step (and the component is therefore over temperature) 604 and initiate a cooling operation to cool the metallic components if the control system determines that the metallic components are heated by the MR signals In a non-limiting example, the acceptable temperature of the surgical tool can be between about 0° C. and about 40° C. when the surgical tool is inserted inside the patient. In another non-limiting example, acceptable increase in temperature of the surgical tool can be between about 2° C. and about 5° C. Other acceptable temperature ranges may be programmed into the control system 40.

At step 606, the control system 40 may determine whether MRI system 14 is operational. For example, the control system 40 may receive output signals from the RF sensor and/or magnetic field detector 200, which are characteristic of an MRI in operation, and which may lead the control system 40 to determine that MRI scanner 14 is operational. At step 608, the control system 40 may initiate a cooling operation if it determines that temperature of at least portions of the surgical tools 32, 34, 36 (such as the distal section 106) or a component thereof, exceeds the predefined threshold, or if the control system 40 determines that the MRI scanner 14 is operational.

In a non-limiting example, the control system 40 may be operatively coupled to a cooling or cryofluid source and may initiate the cooling operation by initiating the supply of the cooling fluid to the surgical tool or to a part thereof, such as the distal portion. The control system may be configured to supply cooling fluid in response to the detection of MR signals or in response to a temperature of a portion or component of the surgical tool being above a predetermined thresh hold; or both.

The system may, for example, comprise at least one temperature sensor for measuring the temperature of the distal section of the cryoprobe, the temperature sensor being operatively coupled to the control system. The control system is configured to supply low pressure cooling fluid in response to receiving the temperature measured by the temperature sensor. The control system may be configured to communicate with the temperature sensor to initiate a temperature measurement of a portion of the surgical tool, such as the distal section, receive measured temperature from the temperature sensor, determine whether the temperature exceeds the predefined threshold; and communicate with the low pressure cooling fluid source to initiate supply of the cooling fluid. The temperature sensor may usefully be further configured to measure the temperature of the distal section when the cooling fluid is supplied by the low pressure cooling fluid source.

Referring to FIG. 1 for illustrative purposes, the cooling fluid can be the same fluid as the cryofluid, and may be stored in the same fluid source 60, but may be delivered at non-cryogenic temperatures and/or pressures to cool the cryoprobe or a component thereof and at cryogenic temperatures/pressures to freeze a patients tissue. In such cases, the cooling fluid may be supplied using a low pressure line 210, and may be conveyed by set of fluid connection lines 62, 64, 66, 68 to the surgical tool. The control system 40 may communicate with a fluid controller 212 (e.g., valve, solenoid, etc.) that can open or close to fluidly connect the cryofluid source 60 to the fluid connection lines 62, 64, 66, 68. In such examples, the surgical tool may be a cryoprobe 100 configured to perform cryoablation and may have a cryocooler positioned at its distal operating tip 104 (as described with respect to FIG. 2). The cooling fluid can thus be supplied using the same fluid lines as the cryofluid. Accordingly, the cooling fluid may travel through the set of fluid lines 62, 64, 66, 68, cryofluid supply 112, and out of the cryocooler (e.g., Joule Thomson orifice) and thereby cool the distal operating tip 104 of the cryoprobe 100. Alternatively, the cooling fluid can be the same as the cryofluid or a different fluid and may be fluidly connected to the surgical tools using existing and/or different fluid paths.

In a non-limiting example, the control system 40 may determine whether MRI scanner 14 is operational, for example by detecting an RF signal or a magnetic field characteristic of an MRI system in operation, or if temperature has exceeded predetermined threshold, only during placement of the surgical tool inside the patient. Alternatively, the control system 40 may make such determinations and initiate cooling procedure before the procedure or intermittently at any desirable times. However, in another non-limiting example, the control system 40 may not continuously supply cooling fluid so as to conserve the amount of cooling fluid supplied (for instance, at times when there is no discernable temperature increase associated with the surgical tool or if the MRI system is not operational).

In certain embodiments, the cryofluid and the cooling fluid can be different fluids so as to not cause unintentional iceball formation. Alternatively, the cryofluid and the cooling fluid can be the same fluid, however, the cooling fluid can be supplied at a significantly lower pressure so as to not result in iceball formation or cryoablation. In such examples, the cooling fluid may simply produce a desired degree of cooling (e.g., by 5° C.) without causing any damage to tissue (particularly healthy tissue, if the cooling procedure is done during probe placement to a target site). In a non-limiting example, the cryofluid may be supplied at a first pressure through the first pressure line 214, and the cooling fluid may be supplied at a second pressure through the second pressure line 210, whereby the first pressure is greater than the second pressure. For instance, the first pressure can be between about 1000 psi and about 4000 psi, for example, about 3500 psi, whereas the second pressure can be less than about 500 psi, although it must be sufficient to ensure cryofluid flow to the tip of the cryoprobe Further, in such examples, the cooling fluid can be argon, and the cryofluid can either be argon at a higher pressure, or a different cryofluid. In examples where the cooling fluid and the cryofluid are both argon, the cryofluid may be supplied through the first pressure line 214 at a pressure of about 3500 psi. Optionally, a pressure regulator may be provided at the first pressure line 214 to deliver the cryofluid at a pressure of about 3500 psi. The cryofluid may be at cryogenic temperatures when expanding from a pressure of about 3500 psi. However, the cooling fluid can also be argon, but supplied through the second pressure line 210 through a flow controller 212 (which may be a valve or solenoid fluidly coupled to a pressure regulator) so as to provide the cooling fluid at a pressure of about 500 psi. Therefore, the cooling fluid may be at significantly higher temperatures than the cryofluid and may not necessarily undergo cryogenic expansion when exiting through the cryocooler (e.g., J-T orifice). In other examples, the first pressure can correspond to pressures at which the cooling fluid has substantial Joule-Thomson cooling, while the second pressure can correspond to pressures at which low or no Joule-Thomson cooling is observable. The second pressure can correspond to a pressure sufficient to supply the cooling fluid to the distal section of the probe to counteract radiofrequency heating.

In certain examples, the control system 40 may intelligently determine the quantity of cooling fluid and/or the duration and frequency over which the cooling fluid is to be supplied. In some such embodiments, the temperature sensor can continue measuring the temperature of portions of the surgical tool (e.g., the distal section 106 of the cryoprobe 100 seen in FIGS. 2 and 3) when the cooling fluid is supplied, and may communicate the temperature measurement to the control system 40. The control system 40 may determine whether a desired temperature reduction of the portion of the surgical tool has been achieved based on the temperature measured by the temperature sensor. In such cases, a desired temperature reduction may be between about 2° C. and about 8° C. Alternatively, the control system 40 can determine the duration over which the cooling fluid is to be supplied as corresponding to time intervals over which the temperature of the portions of the surgical tool exceeds the predefined threshold, and/or time intervals over which the MRI scanner 14 generates MR signals 202 (as detected by the RF sensor and/or magnetic field detector 200).

In another non-limiting example, the control system 40 can determine a first quantity of heat to be removed from the portion of a surgical tool and a first flow rate of the cooling fluid required to remove the first quantity of heat. In such cases, the first quantity of heat can correspond to temperature increase (e.g., as measured by the temperature sensor) over the predefined threshold. In a further advantageous aspect, the control system 40 can predict an increase in temperature over the predefined threshold when the surgical tool is inserted into the patient and/or when MR signals 202 are detected. Accordingly, the control system 40 can determine a second quantity of heat corresponding to the predicted increase in temperature over the predefined threshold and a second flow rate of the cooling fluid required to remove the second quantity of heat from the distal section 106.

As mentioned previously, besides heating surgical tools 32, 34, 36, MR signals 202 from the MRI scanner 14 may introduce other reactive effects in certain components of the surgical system. The surgical tool may be exposed to MR signals 202 of large magnitudes that may induce current flow therethrough that may affect resistance and/or temperature measurement performed by the temperature sensor and/or other components of the electrical heater 116. Additionally, large induced currents from MR signals 202 may affect the identification circuitry or any electronic chip present. For instance, such currents may end up overwriting and/or permanently erasing the data storage medium of the electronic chip 120. Such effects are referred to as reactive electrical signals. Accordingly, to protect components of the surgical system, the control system 40 may perform additional mitigation steps.

FIG. 7 is an example of one such mitigation procedure 700 that can be performed by the control system 40 for example as shown in FIG. 1. In an example, the surgical procedure may be a cryoablation and/or cauterization using a cryoprobe. With reference to FIGS. 1 and 7, the mitigation procedure 700 can be performed intermittently or continuously. Further, the mitigation procedure can be performed prior to, or shortly after the time when the control system 40 communicates with the temperature sensor to measure temperature of the distal section 106 of a cryoprobe 100. Such measurement may be carried out whilst the cryoprobe is inserted into the patient or before. Alternatively, the mitigation procedure 700 can be performed at any desirable time, and may be made, for example, in the absence of temperature measurement. At step 702, the RF sensor and/or magnetic field detector 200 detect MR signals 202 (e.g., radiofrequency or magnetic field 202) associated with the MRI scanner in operation 14, and an output signal is sent to the control system 40. At step 704, the control system 40 checks whether any output signals were received from the RF sensor and/or magnetic field detector 200, and determines that the MRI scanner 14 is operational if output signals were received. At step 706, the control system 40 may then ignore signals or readings, such as reactive electrical signals, associated with electrical components of surgical tool such as cryoprobes or may ignore only certain signals or readings if the control system determines that the MR system is generating MR signals or if the signal or readings are determined to be due to the effects of the MR signals on the electrical components. Alternatively the control system may only accept or process signals or readings that will not be affected by the MR effects. The control system may for example ignore certain signals or readings received from an electrical heater 116. For instance, the control system 40 ignores signals or readings that correspond to faults in the electrical heater 116 optionally however, signals that correspond to electrical resistance of the heater 116 may continue to be received, while other signals associated with the electrical heater 116 may be ignored. In this way temperature measurements determined from the electrical resistance of the heater remain unaffected by the MR signals. Similar approaches may be applied to temperature sensors that are configured to measure the temperature of the cryoprobe or any of its components. At step 708, the control system 40 ignores any other electrical signals associated with the electrical components of the surgical tool (e.g., electrical signals associated with the electronic chip 120 of the surgical tool). Advantageously, the mitigation procedure may improve the accuracy of temperature measurement by ignoring any false electrical signals associated with the cryoprobe 100.

FIG. 8 is another example mitigation procedure 800 that can be performed by the control system 40 for a surgical tool such as a cryoprobe. The mitigation procedure 800 can be suitable, for instance, in situations where merely ignoring electrical signals from the surgical tool may not be sufficient. For example, large induced currents from MR signals, such as RF or magnetic fields 202 may overwrite and/or permanently erase the data storage medium of the electronic chip 120, or otherwise destroy the electrical components of the surgical tool. Accordingly, the controller can electrically disconnect and/or isolate certain portions of the surgical tool, such as an electrical heater, temperature sensor or a chip, so as to eliminate flow of induced currents therethrough.

As was the case with mitigation procedure 700 shown in FIG. 7, mitigation procedure 800 shown in FIG. 8 can be performed intermittently prior to, or shortly after the time when the control system 40 (as seen in FIG. 1) communicates with the temperature sensor to measure temperature of the distal section 106 of a cryoprobe 100 (shown in FIGS. 2 and 3). Such measurement may be carried out whilst the cryoprobe is inserted into the patient or before. Alternatively, the mitigation procedure 800 shown in FIG. 8 can be performed at any desirable time. Referring to FIGS. 1 and 8, at step 802, the RF sensor and/or magnetic field detector 200 detect radiofrequency or magnetic field 202, collectively referred to as MR signals 202 associated with the MRI scanner 14, and an output signal is sent to the control system 40. At step 804, the control system 40 checks whether any output signals were received from the RF sensor and/or magnetic field detector 200, and determines that the MRI system 14 is operational if output signals were received. At step 806, if the control system 40 determines that the MRI scanner 14 is operational, the control system 40 electrically disconnects at least portions of the surgical tool so as to mitigate reactive effects such as induced currents introduced by MR signals 202.

FIG. 9 is a non-limiting exemplary electrical schematic that illustrates circuitry for performing electrical disconnection of portions of the surgical tool. As seen in FIG. 9, the control system 40 may be electrically connected to an electrical switch 900 (e.g., a multiplexer), positioned in electrical communication (e.g., by electrical communication lines 59) with the one or more surgical tools 32, 34, 36. The control system 40 can also be connected to a low-impedance electrical line 902, having impedance lower than impedance of the electrical lines 59 in communication with the surgical tools 32, 34, 36. According to an example, if the control system 40 determines that the MRI system is operational (e.g., based on MR signals 202 detected), the control system 40 can communicate with the electrical switch 900 so as to electrically disconnect the electrical connection between the surgical tool and the control system 40. In the example of FIG. 9, this can be accomplished by "open circuiting" the electrical circuit associated with the surgical tool, and/or "short circuiting" the electrical connection of the control system 40 with the low impedance electrical line. When exposed to the MR signals 202, as the surgical tool is in an open circuit, induced currents may not flow therethrough, thereby protecting electrical components of the surgical tool (e.g., electronic chip 120 and optionally, the electrical heater 116 shown in FIGS. 2 and 3). Returning to FIG. 9, additionally, if the electrical switch 900 short circuits the control system 40, induced currents would be encouraged to flow through the low impedance line instead of the higher impedance electrical line of the surgical tool.

Embodiments of the present disclosure provide one or more advantages. Systems and methods disclosed herein can intelligently detect operation of the MRI system and decide whether mitigation steps are to be performed. In such cases, systems and methods described herein can perform mitigation steps to reduce heating of surgical tools when exposed to MR signals. Systems and methods described herein can also electrically disconnect at least portions of the surgical tool so as to protect certain electrical components of the surgical tool. Additionally, systems and methods described herein can also ignore electrical signals received from the surgical tool so as to not receive false data (e.g., temperature measurements). Systems and methods disclosed herein therefore permit usage of surgical tools having electrical and metal components in conjunction with a MRI system.

Various examples have been described. These and other examples are within the scope of the following claims.

The invention claimed is:

1. A cryoablation system, comprising:
a cryoprobe comprising:
a probe shaft having a distal section insertable into a patient tissue of a patient,
a cryofluid supply within the probe shaft, the cryofluid supply being configured to receive cryofluid, and to supply the cryofluid toward the distal section for cooling and/or freezing the patient tissue, the cryofluid being at cryogenic temperatures when supplied in the cryofluid supply at a first pressure;
a low-pressure cooling fluid source configured to supply a cooling fluid at a second pressure toward the distal section through the cryofluid supply, the second pressure being less than the first pressure,
the low-pressure cooling fluid source being configured to supply the cooling fluid so as to cool the distal section of the cryoprobe when a temperature of a portion of the distal section or a component of the cryoprobe exceeds a predefined threshold, or following detection of a magnetic resonance imaging (MRI) system in operation, whereby cooling provided by the cooling fluid counteracts radiofrequency heating associated with the MRI system.

2. The cryoablation system of claim 1, further comprising:
one or more detectors positioned proximal to the MR system and configured to detect MR signals; and
a control system operatively connected to the one or more detectors, the control system being configured to control the supply of the cooling fluid to the distal section of the cryoprobe in response to the detection of MR signals.

3. The cryoablation system of claim 2, further comprising a temperature sensor for measuring the temperature of the distal section of the cryoprobe, the temperature sensor being operatively coupled to the control system, the control system is configured to supply the cooling fluid in response to receiving the temperature measured by the temperature sensor.

4. The cryoablation system of claim 3 wherein the control system is operatively coupled to the low-pressure cooling fluid source, the control system being configured to:
communicate with the temperature sensor to initiate a temperature measurement of the distal section;
receive measured temperature from the temperature sensor;
determine whether the temperature exceeds the predefined threshold; and
communicate with the low-pressure cooling fluid source to initiate supply of the cooling fluid.

5. The cryoablation system of claim 4, wherein the temperature sensor is further configured to measure the temperature of the distal section when the cooling fluid is supplied by the low-pressure cooling fluid source.

6. The cryoablation system of claim 1, wherein a magnetic resonance (MR) imaging system is positioned in an MR room, the MR signals being associated with the MRI system, the cryoablation system being positionable in the MR room and operational in conjunction with the MRI system.

7. The cryoablation system of claim 2, wherein the control system is configured to determine a duration over which the cooling fluid from the low-pressure cooling fluid source is to be supplied, the duration corresponding to time intervals over which the temperature of the distal section exceeds the predefined threshold, and/or time intervals over which the MRI system generates MR signals.

8. The cryoablation system of claim 2, wherein the control system is configured to initiate supply of the cooling fluid during insertion of the cryoprobe into the patient tissue.

9. The cryoablation system of claim 3, wherein the control system is configured to determine a first quantity of heat to be removed from the distal section of the probe shaft, the first quantity of heat corresponding to measured temperature increase over the predefined threshold, the control system being further configured to determine a first flow rate of the cooling fluid required to remove the first quantity of heat from the distal section.

10. The cryoablation system of claim 9, wherein the control system is configured to predict an increase in temperature over the predefined threshold when the cryoprobe is inserted into the patient and/or when MR signals are detected, and configured to determine a second quantity of heat to be removed from the distal section of the probe shaft, the second quantity of heat corresponding to the predicted increase in temperature over the predefined threshold, the control system being further configured to determine a second flow rate of the cooling fluid required to remove the second quantity of heat from the distal section.

11. The cryoablation system of claim 1, wherein the cooling fluid is argon.

12. The cryoablation system of claim 1, wherein the second pressure is less than about 500 psi.

13. The cryoablation system of claim 11, wherein the cooling fluid is supplied over a duration so as to result in a temperature drop of the distal section between about 2° C. and about 8° C.

14. The cryoablation system of claim 1, wherein the cryofluid is the same fluid as the cooling fluid.

* * * * *